United States Patent
Schreiber

(10) Patent No.: US 11,369,331 B2
(45) Date of Patent: Jun. 28, 2022

(54) METHOD FOR ARTIFACT REDUCTION IN A MEDICAL IMAGE DATA SET, X-RAY DEVICE, COMPUTER PROGRAM AND ELECTRONICALLY READABLE DATA CARRIER

(71) Applicant: Siemens Healthcare GmbH, Erlangen (DE)

(72) Inventor: Bernd Schreiber, Forchheim (DE)

(73) Assignee: Siemens Healthcare GmbH, Erlangen (DE)

( * ) Notice: Subject to any disclaimer, the term of this patent is extended or adjusted under 35 U.S.C. 154(b) by 105 days.

(21) Appl. No.: 16/721,871

(22) Filed: Dec. 19, 2019

(65) Prior Publication Data
US 2020/0196974 A1    Jun. 25, 2020

(30) Foreign Application Priority Data
Dec. 20, 2018 (DE) .......................... 102018222592.3

(51) Int. Cl.
*A61B 6/00* (2006.01)
*G06T 7/00* (2017.01)
*A61B 6/03* (2006.01)

(52) U.S. Cl.
CPC ............ *A61B 6/5258* (2013.01); *A61B 6/032* (2013.01); *G06T 7/0012* (2013.01);
(Continued)

(58) Field of Classification Search
None
See application file for complete search history.

(56) References Cited

U.S. PATENT DOCUMENTS 5,987,347 A * 11/1999 Khoury ..................... G06T 5/20
                                                        600/425
8,233,586 B1 * 7/2012 Boas ....................... G06T 5/002
                                                        378/207
(Continued)

FOREIGN PATENT DOCUMENTS

JP            2010099114 A  *  5/2010  ........... A61B 6/5258

OTHER PUBLICATIONS

Machine translation of JP-2010099114-A (Year: 2010).*
(Continued)

*Primary Examiner* — Vu Le
*Assistant Examiner* — Courtney Joan Nelson
(74) *Attorney, Agent, or Firm* — Lempia Summerfield Katz LLC

(57) ABSTRACT

A method for the reduction of streak artifacts in an image data set reconstructed from projection images of an X-ray device is provided. The method includes determining a first interim data set by applying a non-linear low-pass filter to pixels that satisfy a selection condition. A second non-linear, high-pass-filtered interim data set is determined by pixel-by-pixel subtraction of the first interim data set from the image data set. The second interim data set is Fourier transformed in order to obtain a spatial frequency data set. Frequency portions attributable to artifacts in the spatial frequency data set are removed, and the processed spatial frequency data set is inverse Fourier transformed, such that a third interim data set is obtained. An artifact-reduced result data set is determined by addition of the third interim data set and the first interim data set.

19 Claims, 4 Drawing Sheets

(52) U.S. Cl.
CPC ............... *G06T 2207/10081* (2013.01); *G06T 2207/20028* (2013.01); *G06T 2207/20056* (2013.01); *G06T 2207/20182* (2013.01); *G06T 2207/30004* (2013.01)

(56) References Cited

U.S. PATENT DOCUMENTS

| | | | | |
|---|---|---|---|---|
| 2006/0222261 | A1* | 10/2006 | Archer | G06V 10/431 |
| | | | | 382/280 |
| 2015/0078507 | A1* | 3/2015 | Kyriakou | G06T 5/002 |
| | | | | 382/130 |
| 2015/0279084 | A1* | 10/2015 | Deuerling-Zheng | G06T 5/50 |
| | | | | 345/424 |

OTHER PUBLICATIONS

Meyer, E., Raupach, R., Lell, M., Schmidt, B., & Kachelrieb, M. (2012). Frequency split metal artifact reduction (FSMAR) in computed tomography. Medical Physics, 39(4), 1904-1916. (Year: 2012).*

* cited by examiner

METHOD FOR ARTIFACT REDUCTION IN A MEDICAL IMAGE DATA SET, X-RAY DEVICE, COMPUTER PROGRAM AND ELECTRONICALLY READABLE DATA CARRIER

This application claims the benefit of German Patent Application No. 10 2018 222 592.3, filed on Dec. 20, 2018, which is hereby incorporated by reference in its entirety.

BACKGROUND

The present embodiments relate to reduction of streak artifacts in a three-dimensional (3D) image data set.

The reconstruction of 3D image data sets from projection images acquired with different acquisition geometries (e.g., different projection angles) is a technique used frequently in medical X-ray imaging in order to obtain highly accurate information about the insides of a patient (e.g., information that is suitable for diagnostic purposes). Specifically-provided computed tomography devices may be used in order to determine the three-dimensional image data set, where by contrast, other X-ray devices are increasingly being used to acquire three-dimensional image data sets (e.g., in the case of X-ray devices with a C-arm on which an X-ray tube assembly and an X-ray detector are arranged opposite one another). C-arm X-ray devices of this type, which in some cases may also be embodied specifically as angiography devices, may also be used in the course of a surgical (e.g., minimally invasive) intervention and/or in those instances where a computed tomography device cannot be used for various reasons.

What are known as streak artifacts represent one problem in the evaluation of reconstructed three-dimensional image data sets of a patient. If streak artifacts are present in a reconstructed three-dimensional image data set, it may become problematic for a diagnostician reliably to identify low-contrast details, such as bleeding, a tumor, and/or an area of infarction. This is especially applicable in the case of cone-beam computed tomography using X-ray devices with a C-arm, since the intended use of these systems, in the context of a surgical intervention, for example, provides that there is no real optimization for three-dimensional imaging (e.g., with regard to the patient support, which may include a mattress). In addition, outside of interventions, but in the vicinity thereof, for example, objects that are external to the patient, such as cables or the like, may also be present in the acquisition region. Like imperfections with regard to the other embodiments of the X-ray device, the objects may lead to streak artifacts. Streak artifacts may also occur if non-optimal possibilities for three-dimensional acquisition cause the gaps in the measured projection angles of the projection images to be relatively large (e.g., if a compromise must be accepted in order to reduce the acquisition time).

Streak artifacts typically manifest as highly frequently-occurring, alternating areas of elevated or reduced image values.

SUMMARY AND DESCRIPTION

The scope of the present invention is defined solely by the appended claims and is not affected to any degree by the statements within this summary.

The present embodiments may obviate one or more of the drawbacks or limitations in the related art. For example, the reduction of artifacts, such as streak artifacts, in relevant areas of three-dimensional medical image data sets is provided.

One embodiment of a method has the following acts. A first interim data set is determined by applying a non-linear low-pass filter to pixels that satisfy a selection condition that evaluates image values. The selection condition selects a pixel at an image value of the pixel lying within the image value interval. A second non-linear, high-pass-filtered interim data set is determined by pixel-by-pixel subtraction of the first interim data set from the image data set. The second interim data set is Fourier transformed in order to obtain a spatial frequency data set. Frequency portions attributable to artifacts in the spatial frequency data set are removed, and the spatial frequency data set processed in this way is inverse Fourier transformed in order to obtain a third interim data set. An artifact-reduced result data set is determined by addition of the third interim data set and the first interim data set.

The present embodiments determine, using skillful non-linear filtering only in portions of the image data set showing soft tissue, a second interim data set containing the streak artifacts, but containing no or merely minimal contributions of high-contrast objects, for which the contributions to streak artifacts in the frequency range are identifiable and correspondingly removable, without relevant image information inadvertently also being removed in the process. In other words, the second interim data set is specifically determined such that the second interim data set describes essentially only quantum noise and structural noise, specifically streaks in the soft tissue portion of the image data set, whereas other objects or material classes outside of this criterion have no or only a minor influence. This makes it possible to significantly suppress streak artifacts without causing a deterioration in the spatial resolution and/or removing relevant image information (e.g., diagnostically relevant portions) and/or influencing image quality in areas showing high-contrast objects and/or other material classes.

The non-linearity of the low-pass filter, and consequently, also of the high-pass filter formed implicitly for the second interim data set, is extremely important since relatively strong edges, especially in the transition to other material classes (e.g., high-contrast objects), are not influenced by the inventive procedure for artifact reduction. In an embodiment, in the case of low-pass filtering within one filter mask used, pixels lying around a pixel being examined are evaluated as a function of the difference in image value relative to the image value of the pixel being examined, where, for example, more strongly deviating image values result in a weaker weighting, and the filtering process is performed as a function of the evaluation. Additionally or alternatively, a bilateral filter and/or a weighted median filter is used as the low-pass filter. This is based on the knowledge that, in the case of streak artifacts, there is usually no very strong contrast difference within the soft tissue region, since artifacts may also be regarded as a structural noise effect. In any case, the image value differences are clearer relative to other structures (e.g., high-contrast objects such as bones and the like). If the image value difference relative to another pixel lying within the filter mask is too high, a low weighting may be performed, or the filtering process itself may be eliminated. Both of the examples mentioned (e.g., both the bilateral filter and also the weighted median filter) use evaluation mechanisms of this type in any case and are parameterized accordingly.

Specifically, therefore, as part of the non-linearity of the application of the filter, an intensity weighting that applies a penalty to excessive image value differences relative to neighbors (e.g., image value differences that significantly exceed the standard deviation essentially produced by the noise result in the corresponding image values being disregarded or in a significantly lower weighting in the low-pass filtering) is performed. This achieves the outcome that voxels that include soft tissue are not impaired, for example, by other adjacent structures in the immediate vicinity that are still captured by the filter mask used. This avoids edges to the other structures being imaged in the resulting second interim data set and possibly being influenced by the correction procedure for the streak artifacts.

In a development, the present embodiments may also provide that, for example, as an additional selection condition, individual deviating pixels with an image value lying outside the image value interval, which are located within a region in which the image values lie in the image value interval, are detected and also subjected to the filtering. In this way, a type of outlier detection may be created for individual deviating voxels, which may then also be subjected to the filtering.

The first interim data set nevertheless still includes the unfiltered pixels and image values so that these are dispensed with in the subtraction from the image data set in order to determine the second interim data set; therefore, the second interim data set, as explained, includes only the differences revealed by the low-pass filter (e.g., structural noise (streak artifacts) as well as quantum noise and also any structures of the soft tissue still present, so that image content lying outside the soft tissue regions is under no circumstances influenced).

In an embodiment for the removal of frequency portions attributable to artifacts in the spatial frequency data set, the present embodiments also provide that the removal of artifact portions in the spatial frequency data set is performed by threshold value formation, in which frequency portions in the spatial frequency data set that exceed the threshold value are removed. This provides that, with the aid of a threshold value, peaks within the spatial frequency data set that indicate markedly high-frequency artifact structures are detected and "cut". For example, it may therefore be provided that all spatial frequency data lying above the threshold value is replaced with the threshold value, and/or the peak is "cut" (e.g., typical noise is applied). This procedure is essentially based on the knowledge that relevant image information that is actually present in soft tissue regions (e.g., lesions) is usually low frequency and therefore does not produce a peak in the spatial frequency data set corresponding to a noise power spectrum. However, typical streak artifacts form clear peaks that may be identified and detected easily. For example, particularly clear peaks appear in the spatial frequency data set when the patient is positioned on a mattress, and streak artifacts are produced as a result.

In this context, the determination of the threshold value may be performed as a function of the spectrum described by the spatial frequency data set. Thus, it may be provided, for example, that the threshold value is determined from the spatial frequency data set (e.g., as a multiple of a mean value of the spatial frequency values; the fifth to fifteenth multiple). Thus, the threshold value is ultimately defined with the aid of the spectrum itself (e.g., as the tenth multiple of the mean value of the spatial frequency values of the spatial frequency data set). In general, the threshold value is to be selected, possibly also empirically, such that, although artifacts may reliably be eliminated or at least significantly reduced, no image information that is actually present (e.g., diagnostics-relevant image information) is inadvertently removed.

In a development, the image data set may be present as sectional images or slice images. The determination of an associated result image of the result data set is performed successively for at least a portion of the sectional images or slice images. Examining individual sectional images or slice images separately in this way has multiple advantages. First, the artifact reduction described may be reduced down to the sectional images or slice images in which streak artifacts are actually also identified, so that a reduction in the computing effort may already be achieved in this way. For example, in this context, user inputs that describe the sectional images or slice images to be processed may be received via a user interface (e.g., an input apparatus of the X-ray device).

A further advantage of examining two-dimensional partial data sets (e.g., sectional images or slice images) is that a smaller proportion of the image values is examined, and therefore, the likelihood that artifact effects will cancel each other out is reduced. A two-dimensional Fourier transform may be used as the Fourier transform for the two-dimensional second interim data sets derived from a particular sectional image or slice image. A 2D Fourier transform may be performed significantly faster and with significantly lower computing effort than a 3D Fourier transform.

If sectional images or slice images are used as partial data sets of the image data set, the low-pass filtering may also follow in three dimensions (e.g., with a three-dimensional filter mask), since the neighboring voxels that are also perpendicular to the sectional image plane or slice image plane are known. However, excellent results are also achieved with non-linear low-pass filtering performed merely two-dimensionally in the sectional image plane or slice image plane.

In order to reduce quantum noise, the result data set may also be filtered with a further filter (e.g., a bilateral filter). After the streak artifacts have been reduced according to the acts described above, in the context of the present embodiments, it is also possible to strive for a further suppression of quantum noise by, for example, applying a bilateral filter parameterized accordingly, where also, the spatial resolution may not be reduced.

Besides the method, the present embodiments also relate to an X-ray device having a control device configured for performing the method according to the present embodiments. All the embodiments relating to the method may be transferred analogously to the X-ray device, with which the above-mentioned advantages may therefore also be achieved. The X-ray device may be an X-ray device that has a C-arm on which an X-ray detector and an X-ray tube assembly are arranged opposite one another. In one embodiment, C-arm X-ray devices of this type may be used more flexibly (e.g., if the C-arm X-ray devices have a mobile configuration) with respect to monitoring surgical (e.g., minimally invasive) interventions but typically are not optimized for three-dimensional imaging. The streak artifacts may thus occur. The streak artifacts may be easily reduced with the aid of the present embodiments to produce a significantly improved image quality.

The control device may have at least one processor and a storage device. For performing the method according to the present embodiments, in addition to a control unit provided in the control device, as is known in principle, a filter unit for determining the first interim data set, a subtraction unit for determining the second interim data set, a transformation unit for performing the Fourier transforms, an artifact reduction unit for removing frequency portions attributable to artifacts in the spatial frequency data set, and a determination unit for determining the artifact-reduced result data set may be provided. Some or all of these functional units may be realized as image processors.

The result data set may be output via an output unit including, for example, a corresponding output interface. For example, the result data set may be presented on a display apparatus of the X-ray device. The result data set may also be stored for later use.

For example, a computer program according to the present embodiments may be loaded directly into a memory of a computing device (e.g., a control device of an X-ray device) and has program instructions to perform the acts of a method according to the present embodiments when the computer program is executed in the computing device. The computer program may be stored on an electronically readable data carrier (e.g., a non-transitory computer-readable storage medium) according to the present embodiments, which therefore includes electronically readable control information stored thereupon. The electronically readable control information includes at least one computer program according to the present embodiments and is configured to carry out a method of the present embodiments when the data carrier is used in a computing device (e.g., a control device of an X-ray device). The data carrier may be a non-transient data carrier (e.g., a CD-ROM).

DETAILED DESCRIPTION

Figure 1:
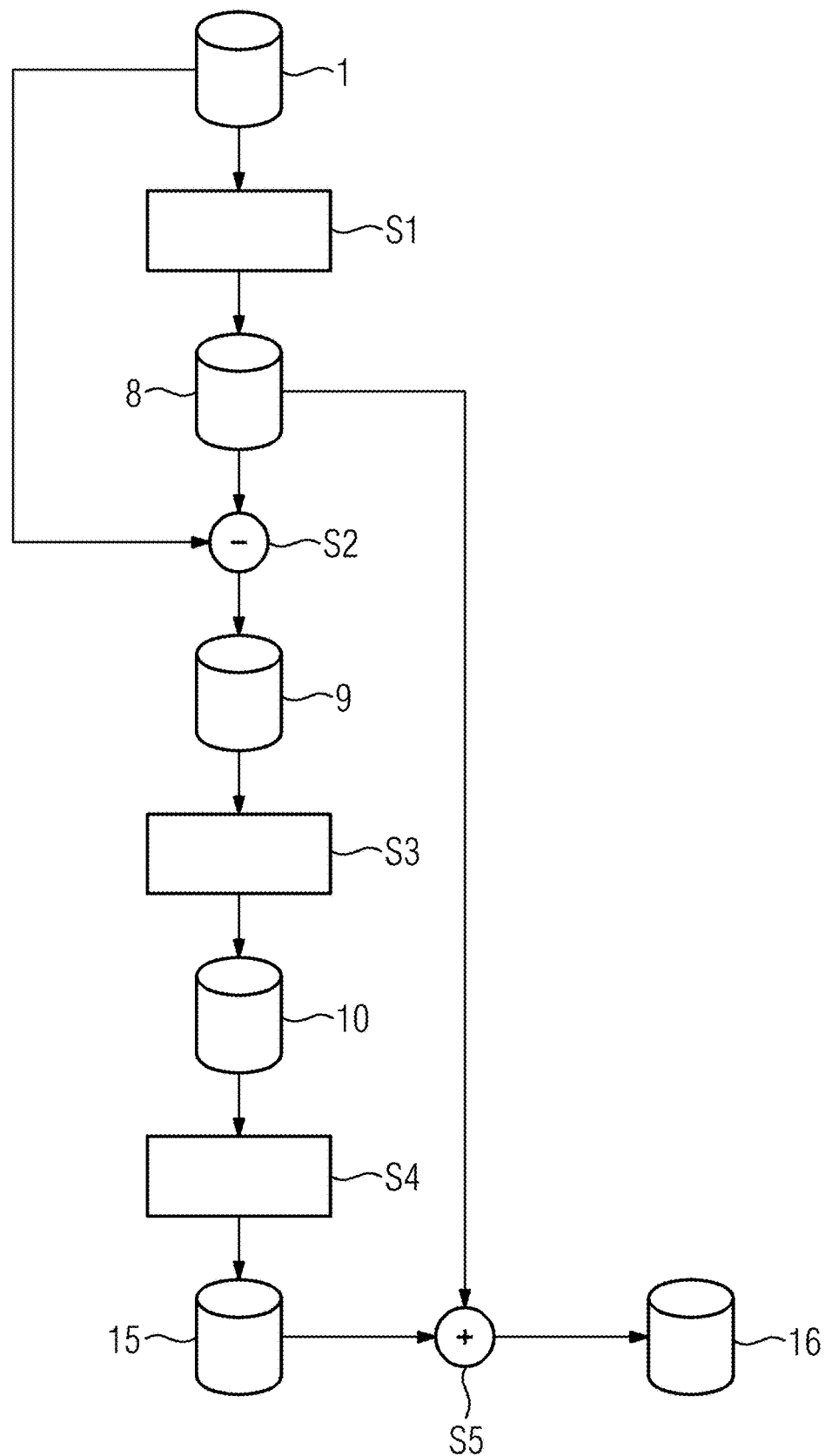
FIG. 1 shows a flow chart of an exemplary embodiment of a method.

FIG. 1 shows a flow chart of an exemplary embodiment of a method, where a patient's head (e.g., the brain as a soft tissue region) is to be examined with three-dimensional (3D) X-ray imaging (e.g., with administration of a contrast agent). For this purpose, projection images of the head as the acquisition region are acquired from different projection angles using an X-ray device with a C-arm (e.g., an angiography device), whereupon from the two-dimensional projection images, a 3D image data set 1 of the acquisition region is reconstructed using known procedures. This forms the starting point for the method described. In principle, the image values (e.g., HU values), at which soft tissue regions in the image data set 1 are typically imaged, are already known. These image values are described by a pre-determined image value interval.

Figure 2:
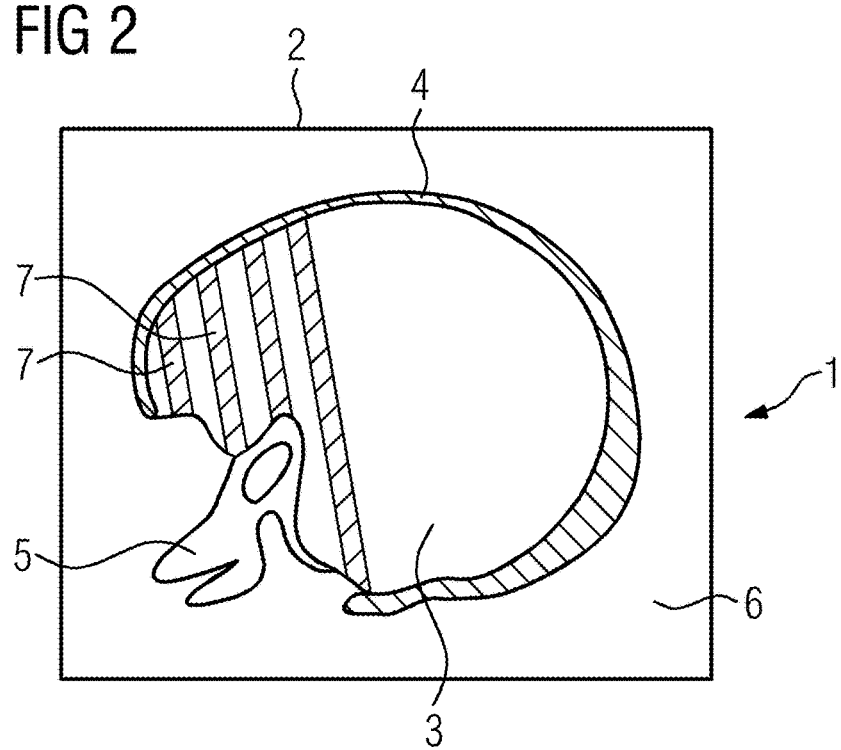
FIG. 2 shows a schematic representation of an exemplary image data set.

FIG. 2 shows a schematic sketch of exemplary content of a 3D image data set 1 of this type, a two-dimensional sectional image 2 of which is shown in the present case by way of example. In the present case, the soft tissue region 3 including the brain is surrounded by a bone region 4 of the skull, as well as further high-contrast bone structures 5 and air regions 6. Further, different structures or objects represented with image values lying outside the image value interval may also include medical instruments, contrast agents, and the like.

As shown in FIG. 2, high-frequency streak artifacts 7 are present in the soft tissue region 3, which may have been produced by, for example, a mattress on which the patient is positioned. Although the streak artifacts 7 do not deviate strongly from the rest of the soft tissue region 3 in terms of image values, the streak artifacts 7 nevertheless disrupt the search for diagnostically relevant, low-contrast details. The exemplary embodiment of the method shown in FIG. 1 deals with the maximum removal of such streak artifacts 7. Here, in act S1, a non-linear low-pass filter is first applied to the image data set 1, but only to pixels with an image value lying in the pre-defined image value interval (e.g., to soft tissue regions 3). In the present case, the non-linear low-pass filter is a bilateral filter or a weighted median filter with which pixels (e.g., voxels) within the filter mask that deviate excessively in image value are weighted significantly lower or omitted completely in the filtering, such that the low-pass filtering then does not act on the edges delimiting the soft tissue regions 3 compared with higher-contrast regions, and instead, merely acts on structures lying in normal regions of structural noise and quantum noise (e.g., the streak artifacts 7). This provides that when the selection condition, which checks whether the image value of the pixel lies in the image value interval, reaches an edge point of a soft tissue region 3, the pixels lying outside the soft tissue region 3 that deviate strongly in image value do not contribute to the filter result or contribute only to a small extent. An additional selection criterion may also deal with individual outliers within soft tissue regions 3 with isolated image values lying outside the image value interval.

The result of act S1 is a first interim data set 8 to which a non-linear low-pass filter has been applied to structures within the soft tissue regions 3, but without influencing other structures in the image data set 1 (e.g., bone regions 4, 5, air regions 6, contrast agent regions, areas of medical apparatus, and the like).

In act S2, the first interim data set 8 is subtracted from the interim data set 1 in order to obtain a second interim data set 9. The second interim data set 9 is then subjected to non-linear high-pass filtering within the soft tissue regions 3 and only includes these structures, and therefore, no bones, air, or the like.

Figure 3:
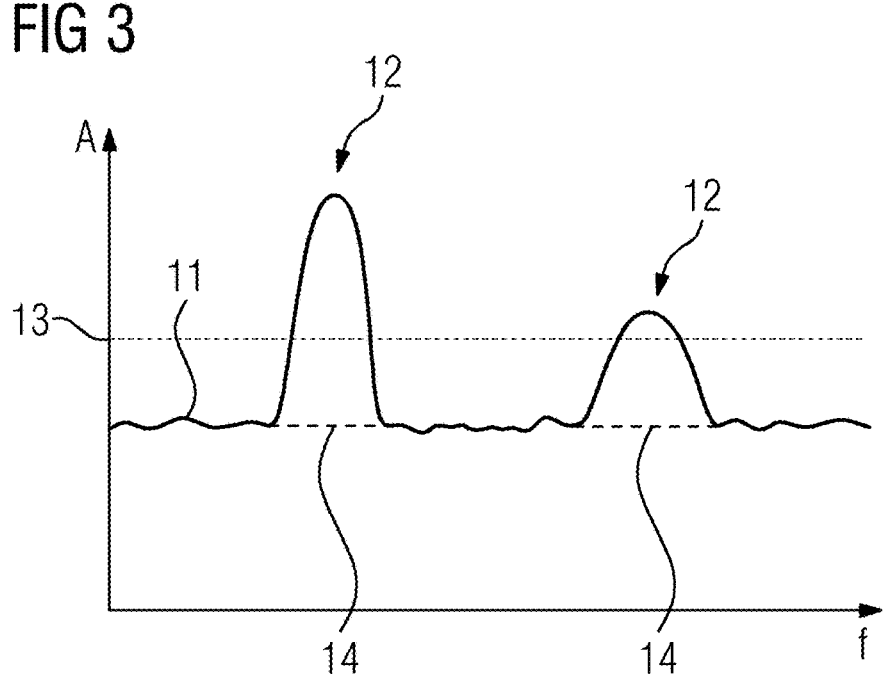
FIG. 3 illustrates an exemplary removal of frequency portions.

The second interim data set 9 is Fourier transformed in act S3 in order to obtain a frequency spatial data set 10 that finally reflects the spatial frequency spectrum of the second interim data set 9. Such a spectrum 11 is shown schematically in FIG. 3. In this spectrum 11, the streak artifacts 7 as well as possibly other artifact structures are shown as clearly identifiable peaks 12 that project clearly over the frequency portions of other structures. By analyzing the spectrum 11 (e.g., the spatial frequency data set 10), a threshold value 13 may be defined, for example, as the tenth multiple of the mean value of the spatial frequency values of the spatial frequency data set 10, where peaks 12 that project over the threshold value 13 may be detected as attributable to artifact structures.

This is used in act S4 to remove the corresponding frequency portions of the peaks 12, and therefore, to "cut" the peaks 12. The spatial frequency values at those points may, for example, be set to the threshold value 13 or may be reduced in entirety to the general noise level, as shown by the dashed lines 14 in FIG. 3.

The spatial frequency data set 10 cleaned in this way is also back-Fourier transformed in act S4 in order to obtain a third interim data set 15 in which the streak artifacts 7 are removed or at least significantly reduced.

As a result, using act S5, in which the third interim data set 15 is added to the first interim data set 8, an artifact-reduced result data set 16 may be obtained.

Figure 4:
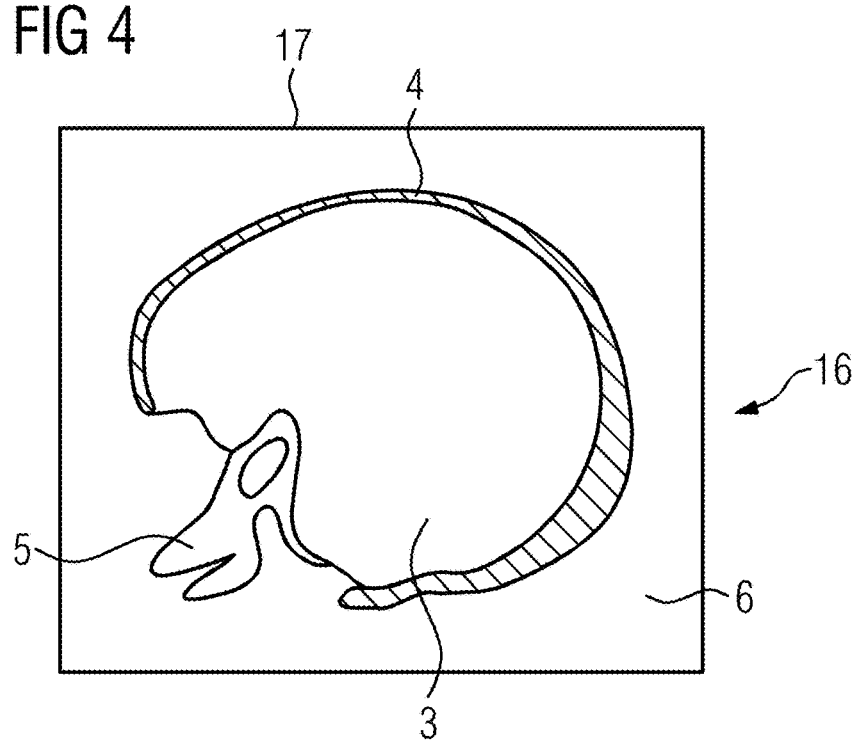
FIG. 4 shows a schematic representation of an exemplary result data set.

As shown by the schematic representation of the artifact-reduced result data set 16, again in the form of a sectional image 17 (e.g., as the result image), in FIG. 4, the streak artifacts 7 are no longer visible.

With reference to the exemplary embodiment in FIG. 1, the procedure described may be performed successively for two-dimensional partial data sets (e.g., sectional images 2 or slice images) of the image data set 1, providing that always just one two-dimensional sectional image 2 or slice image is filtered, transformed, and one result image is obtained as part of the result data set 16 (e.g., the sectional image 17). This may be provided in that only the sectional images or slice images of the image data set 1 that also show relevant streak artifacts 7 are to be processed, for example, after a selection has been made by a user. Computing effort and computing time may also be saved by the two-dimensional Fourier transform requiring less effort to implement than a three-dimensional Fourier transform.

The result data set 16 may be displayed, for example, on a display apparatus of the X-ray device and/or stored in an internal or external storage device (e.g., transferred to a further external computing device).

Figure 5:
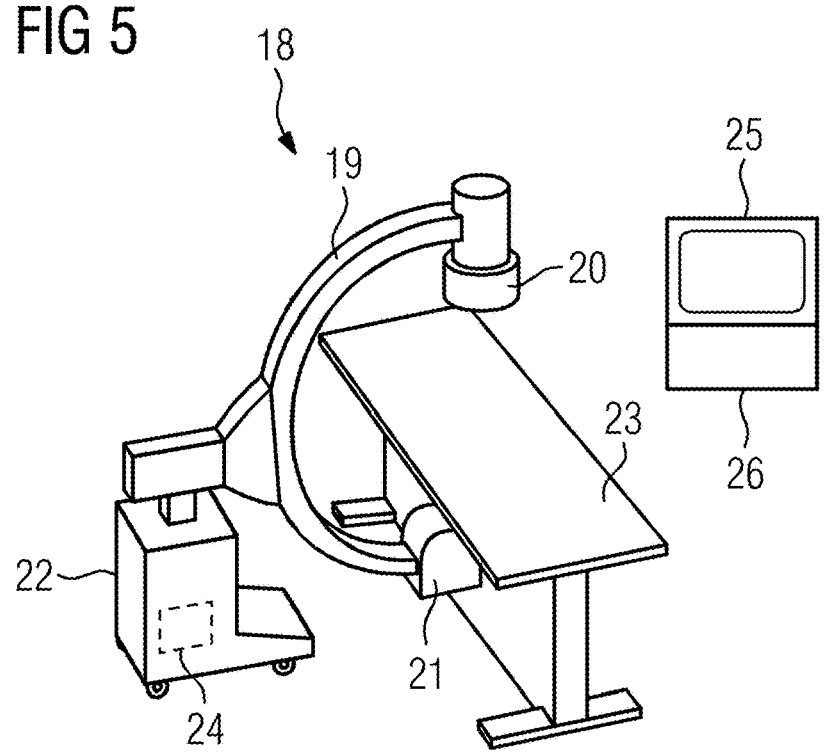
FIG. 5 shows one embodiment of an X-ray device.

FIG. 5 shows an exemplary embodiment of an X-ray device 18 that includes a C-arm 19 on which an X-ray tube assembly 20 and an X-ray detector 21 are arranged opposite one another. A stand 22 is configured to be mobile and may therefore allow the X-ray device 18 to be used at a patient table 23 configured, for example, as an operating table. The movability of the C-arm 19 allows projection images to be acquired from different projection directions.

The operation of the X-ray device 18 is controlled by a control device 24 that is also configured for performing the method according to the present embodiments. A display apparatus 25 (e.g., a visual monitor) may be used to display the result data set 16; an input apparatus 26, by which, by way of example, partial data sets of the image data set 1 (e.g., individual sectional images 2) may be selected for artifact correction in accordance with the method according to the present embodiments, may also be provided.

Figure 6:
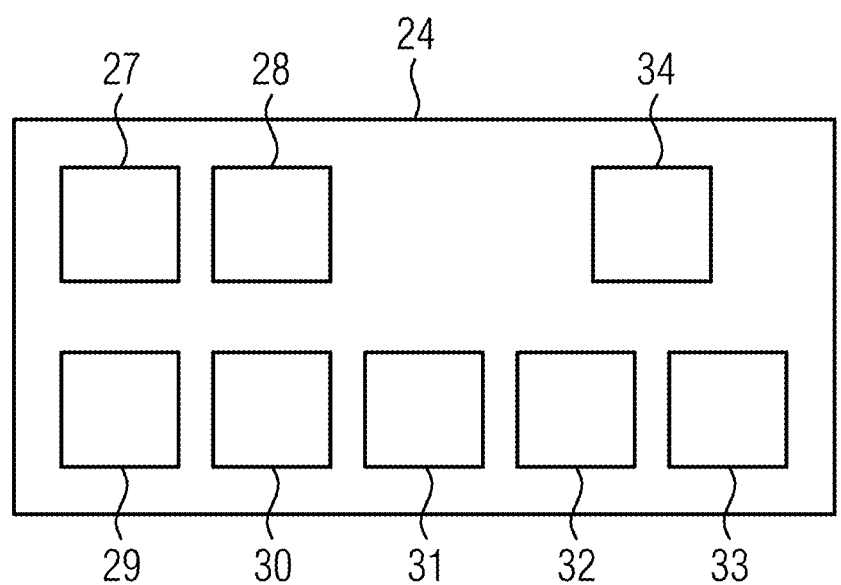
FIG. 6 shows an exemplary functional structure of a control device of the X-ray device.

FIG. 6 shows the functional structure of the control device 24 in more detail. The control device has, as is generally known, an acquisition unit 27 that controls the acquisition operations of the X-ray device 18 and, for example, the acquisition of the projection images. In a reconstruction unit 28 that is likewise sufficiently known in the prior art, the three-dimensional image data set 1 may be reconstructed from the projection images.

For performing the method according to the present embodiments, the control device 24 also has a filter unit 29 for performing act S1, a subtraction unit 30 for performing act S2, a transformation unit 31 for performing the Fourier transforms in acts S3 and S4, an artifact reduction unit 32 for removing frequency portions attributable to artifacts in act S4, and a determination unit 33 for performing act S5. In particular, here the functional units 29, 30, 32 and 33 may be image processors. The control device 24 may also have an output unit 34 that is, for example, configured from or includes an output interface.

Although the invention has been illustrated and described in greater detail on the basis of the exemplary embodiments, the invention is not limited by the disclosed examples. Other variations may be derived herefrom by the person skilled in the art without leaving the scope of protection of the invention.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for reduction of streak artifacts in a three-dimensional (3D) image data set reconstructed from projection images of an X-ray device, wherein the 3D image data set has image values assigned to pixels and shows an acquisition region of the patient having at least one soft tissue region imaged by image values within an image value interval, the method comprising:

determining a first interim data set, the determining of the first interim data set comprising applying a non-linear low-pass filter to pixels of the 3D image data set that satisfy a selection condition that evaluates image values, wherein the selection condition selects a pixel at an image value of the pixel lying within the image value interval, the first interim data set being 3D;

determining a second interim data set, the second interim data set being non-linear and high-pass-filtered, the determining of the second interim data set comprising pixel-by-pixel subtracting of the first interim data set from the 3D image data set, the second interim data set being 3D;

Fourier transforming the second interim data set, such that a spatial frequency data set is obtained;

removing frequency portions attributable to artifacts in the spatial frequency data set and inverse Fourier transforming the spatial frequency data set processed in this way, such that a third interim data set is obtained; and determining an artifact-reduced result data set, the determining of the artifact-reduced result data set comprising adding the third interim data set and the first interim data set.

2. The method of claim 1, wherein the method further comprises evaluating, in the case of low-pass filtering within one filter mask used, pixels lying around a pixel being examined as a function of a difference in image value relative to the image value of the pixel being examined, wherein more strongly deviating image values result in a weaker weighting, and wherein the filtering process is performed as a function of the evaluating, wherein a bilateral filter, a weighted median filter, or the bilateral filter and the weighted median filter are used as the low-pass filter, or a combination thereof.

3. The method of claim 1, wherein removing frequency portions attributable to artifacts in the spatial frequency data set comprises threshold value forming, in which frequency portions in the spatial frequency data set that exceed a threshold value are removed.

4. The method of claim 3, further comprising determining the threshold value from the spatial frequency data set.

5. The method of claim 4, further comprising determining the threshold value from the spatial frequency data set as a multiple of a mean value of the spatial frequency values.

6. The method of claim 5, wherein the multiple of the mean value of the spatial frequency values is the 2nd to 15th multiple.

7. The method of claim 1, wherein the image data set is present as sectional images or slice images,
wherein the method further comprises determining an associated result image of the artifact-reduced result data set successively for at least a portion of the sectional images or the slice images.

8. The method of claim 1, further comprising filtering the artifact-reduced result data set as a whole with a further filter, such that quantum noise is reduced.

9. The method of claim 8, wherein the further filter is a bilateral filter.

10. An X-ray device comprising:
a controller configured to reduce streak artifacts in a three-dimensional (3D) image data set reconstructed from projection images of an X-ray device, wherein the 3D image data set has image values assigned to pixels and shows an acquisition region of the patient having at least one soft tissue region imaged by image values within an image value interval, the reduction of the streak artifacts in the 3D image data set comprising:
determination, by the controller, of a first interim data set, the determination of the first interim data set comprising application of a non-linear low-pass filter to pixels of the 3D image data set that satisfy a selection condition that evaluates image values, wherein the selection condition selects a pixel at an image value of the pixel lying within the image value interval, the first interim data set being 3D;
determination, by the controller, of a second interim data set, the second interim data set being non-linear and high-pass-filtered, the determination of the second interim data set comprising pixel-by-pixel subtraction of the first interim data set from the 3D image data set, the second interim data set being 3D;
Fourier transformation, by the controller, of the second interim data set, such that a spatial frequency data set is obtained;
removal, by the controller, of frequency portions attributable to artifacts in the spatial frequency data set and inverse Fourier transformation of the spatial frequency data set processed in this way, such that a third interim data set is obtained; and
determination, by the controller, of an artifact-reduced result data set, the determination of the artifact-reduced result data set comprising addition of the third interim data set and the first interim data set.

11. In a non-transitory computer-readable storage medium that stores instructions executable by one or more processors to reduce streak artifacts in a three-dimensional (3D) image data set reconstructed from projection images of an X-ray device, wherein the 3D image data set has image values assigned to pixels and shows an acquisition region of the patient having at least one soft tissue region imaged by image values within an image value interval, the instructions comprising:
determining a first interim data set, the determining of the first interim data set comprising applying a non-linear low-pass filter to pixels of the 3D image data set that satisfy a selection condition that evaluates image values, wherein the selection condition selects a pixel at an image value of the pixel lying within the image value interval, the first interim data set being 3D;
determining a second interim data set, the second interim data set being non-linear and high-pass-filtered, the determining of the second interim data set comprising pixel-by-pixel subtracting of the first interim data set from the 3D image data set, the second interim data set being 3D;
Fourier transforming the second interim data set, such that a spatial frequency data set is obtained;
removing frequency portions attributable to artifacts in the spatial frequency data set and inverse Fourier transforming the spatial frequency data set processed in this way, such that a third interim data set is obtained; and
determining an artifact-reduced result data set, the determining of the artifact-reduced result data set comprising adding the third interim data set and the first interim data set.

12. The non-transitory computer-readable storage medium of claim 11, wherein:
the instructions further comprise evaluating, in the case of low-pass filtering within one filter mask used, pixels lying around a pixel being examined as a function of a difference in image value relative to the image value of the pixel being examined, wherein more strongly deviating image values result in a weaker weighting, and wherein the filtering process is performed as a function of the evaluating;
a bilateral filter, a weighted median filter, or the bilateral filter and the weighted median filter are used as the low-pass filter; or
a combination thereof.

13. The non-transitory computer-readable storage medium of claim 11, wherein removing frequency portions attributable to artifacts in the spatial frequency data set comprises threshold value forming, in which frequency portions in the spatial frequency data set that exceed a threshold value are removed.

14. The non-transitory computer-readable storage medium of claim 13, wherein the instructions further comprise determining the threshold value from the spatial frequency data set.

15. The non-transitory computer-readable storage medium of claim 14, wherein the instructions further comprise determining the threshold value from the spatial frequency data set as a multiple of a mean value of the spatial frequency values.

16. The non-transitory computer-readable storage medium of claim 15, wherein the multiple of the mean value of the spatial frequency values is the 2nd to 15th multiple.

17. The non-transitory computer-readable storage medium of claim 11, wherein the image data set is present as sectional images or slice images,
wherein the instructions further comprise determining an associated result image of the artifact-reduced result data set successively for at least a portion of the sectional images or the slice images.

18. The non-transitory computer-readable storage medium of claim 11, wherein the instructions further comprise filtering the artifact-reduced result data set as a whole with a further filter, such that quantum noise is reduced.

19. The non-transitory computer-readable storage medium of claim 18, wherein the further filter is a bilateral filter.

\* \* \* \* \*